US012594248B2

(12) United States Patent  (10) Patent No.: US 12,594,248 B2
Sobel et al.  (45) Date of Patent: Apr. 7, 2026

(54) STRESS MANAGEMENT IN HUMAN SUBJECTS IN NEED THEREOF

(71) Applicant: YEDA RESEARCH AND DEVELOPMENT CO. LTD., Rehovot (IL)

(72) Inventors: Noam Sobel, Yafo (IL); Eva Mishor, Rehovot (IL); Yaara Endevelt-Shapira, Rehovot (IL); Shiri Karagach, Rehovot (IL); Yaniv Mama, Rehovot (IL); Yigal Sharon, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 838 days.

(21) Appl. No.: 17/758,839

(22) PCT Filed: Jan. 13, 2021

(86) PCT No.: PCT/IL2021/050038
§ 371 (c)(1),
(2) Date: Jul. 14, 2022

(87) PCT Pub. No.: WO2021/144792
PCT Pub. Date: Jul. 22, 2021

(65) Prior Publication Data
US 2023/0050605 A1  Feb. 16, 2023

Related U.S. Application Data

(60) Provisional application No. 62/960,759, filed on Jan. 14, 2020.

(51) Int. Cl.
*A61K 31/11* (2006.01)
*A61K 9/00* (2006.01)
*A61P 25/20* (2006.01)

(52) U.S. Cl.
CPC .............. *A61K 31/11* (2013.01); *A61K 9/007* (2013.01); *A61P 25/20* (2018.01)

(58) Field of Classification Search
CPC .................................................... A61K 31/11
See application file for complete search history.

(56) References Cited

U.S. PATENT DOCUMENTS

2008/0031907 A1* 2/2008 Tamarkin ................ A61P 17/00
514/183

OTHER PUBLICATIONS

XXVIIth Annual Meeting of the European Chemoreception Research Organization, ECRO 2017, Chemical Senses, vol. 43, Issue 3, Mar. 2018, pp. e1-e36, Published: Feb. 26, 2018, available at https://academic.oup.com/chemse/article/43/3/e1/4910404.*
XXVth Annual Meeting of the European Chemoreception Research Organization, ECRO 2015, Chemical Senses, vol. 41, Issue 4, May 2016, pp. 379-435, Published: Apr. 21, 2016, available at https://academic.oup.com/chemse/article/41/4/379/2366142.*
Klein et al., Activation of the mouse odorant receptor 37 subsystem coincides with a reduction of novel environment-induced activity within the paraventricular nucleus of the hypothalamus, Eur J Neurosci, Mar. 2015;41(6):793-801.*
Chandel et al., Recent advances in aerosolised drug delivery, Biomedicine & Pharmacotherapy, vol. 112, Apr. 2019, 108601.*
Endevelt-Shapira et al., Altered responses to social chemosignals in autism spectrum disorder, Nat Neurosci, Jan. 2018;21(1):111-119.*
Bautze, et al., Mammalian-Specific OR37 Receptors Are Differentially Activated by Distinct Odorous Fatty Aldehydes, Chem. Senses, 37:479-493 (2012).
XXVIIth Annual Meeting of the European Chemoreception Research Organization, ECRO 2017, Chem. Senses, 43:e1-e36 (2018).
XXVth Annual Meeting of the European Chemoreception Research Organization, ECRO 2015, Chem. Senses, 41:379-435 (2016).
Daan Van Nieuwenburg et al., "The Subtle Signaling Strength of Smells: A Masked Odor Enhances Interpersonal Trust", Front Psychol., vol. 10, No. 1890, pp. 1-10 (Aug. 2019).
Bettina Klein et al.: "Activation of the mouse odorant receptor 37 subsystem coincides with a reduction of novel environment-induced activity within the paraventricular nucleus of the hypothalamus", Eur. J. Neurosci., vol. 41, No. 6, pp. 793-801 (Jan. 2015).
Yaara Endevelt-Shapira et al.: "Altered responses to social chemosignals in autism spectrum disorder", Nat. Neurosci., vol. 21, No. 1, pp. 111-119 (Nov. 2017).

* cited by examiner

*Primary Examiner* — Svetlana M Ivanova
(74) *Attorney, Agent, or Firm* — FISHERBROYLES, LLP; Roger L. Browdy

(57) ABSTRACT

The present invention discloses uses of hexadecanal in managing stress.

9 Claims, 3 Drawing Sheets

STRESS MANAGEMENT IN HUMAN SUBJECTS IN NEED THEREOF

FIELD OF THE INVENTION

The present invention generally relates to stress management in human subjects.

BACKGROUND OF THE INVENTION

Stress is a psychological state of mind, which occurs in various situations and is triggered by various causes. The causes of stress vary between subjects and the stress response can vary as well. There have been experiments which attempt to measure stress by physiological indicators. However, due to various reasons including the variability in stress response and stress triggers, the correlation between stress and various physiological indicators such as heart rate were found to be poor indicators of stress. Thus, psychological indicators for stress are more reliable and while they may be subjective, they are reliable and directly linked to stress.

Klein et al [15] studied and reported on the mouse OR37 receptor subtypes A, B and C which were shown to be activated by the long-chain aliphatic aldehydes pentadecanal, hexadecanal and heptadecanal, respectively. The search for biological sources of these compounds showed that bodily secretions from conspecifics activated the OR37A, B and C glomerulus. At the same time, the activity of cells in a target region of projection neurons from OR37 glomeruli, the paraventricular nucleus of the hypothalamus (PVN), was reduced compared with controls (clean test box). A large number of the activated cells in the PVN of mice that were placed into a clean test box were corticotropin-releasing hormone cells, indicating an induction of the stress axis due to the novel environment. The much lower number of activated cells of mice in a box enriched with bodily secretions from conspecifics indicated a reduced stress response. As bodily secretions from conspecifics activated the OR37 system and simultaneously reduced stress-induced activation of the PVN, it was tested whether the ligands for OR37 receptors could induce this effect. Indeed, a similarly reduced activity in the PVN was found in mice kept in a clean test box and exposed to a mixture of the OR37 ligands delivered via an air stream. These data indicate that the OR37 system may play a role in mediating a phenomenon called social buffering.

It is important to understand the differences between various states of mind which are often linked to stress. Aggression, arousal, fear may be mistakenly interpreted as stress or mistakenly linked to stress.

REFERENCES

1. R. Mykytowycz, B. Goodrich, Skin glands as organs of communication in mammals. *Journal of Investigative Dermatology* 62, 124-131 (1974).
2. M. Novotny, S. Harvey, B. Jemiolo, J. Alberts, Synthetic pheromones that promote inter-male aggression in mice. *Proceedings of the National Academy of Sciences* 82, 2059-2061 (1985).
3. P. Chamero et al., Identification of protein pheromones that promote aggressive behaviour. *Nature* 450, 899 (2007).
4. D. M. Ferrero et al., A juvenile mouse pheromone inhibits sexual behaviour through the vomeronasal system. *Nature* 502, 368-371 (2013).
5. U. SHANAS, J. TERKEL, Mole-rat harderian gland secretions inhibit aggression. *Animal behaviour* 54, 1255-1263 (1997).
6. S. Gelstein et al., Human tears contain a chemosignal. *Science* 331, 226-230 (2011).
7. T. J. Oh, M. Y. Kim, K. S. Park, Y. M. Cho, Effects of chemosignals from sad tears and postprandial plasma on appetite and food intake in humans. *PloS one* 7, e42352 (2012).
8. J. J. McGlone, S. E. Curtis, E. M. Banks, Evidence for aggression-modulating pheromones in prepuberal pigs. *Behavioral and neural biology* 47, 27-39 (1987).
9. N. Chernyak, K. Leimgruber, Y. Dunham, J. Hu, P. Blake, Paying back those who harmed us but not those who helped us: Direct negative reciprocity precedes direct positive reciprocity in early development. (2019).
10. J. R. Fanning, S. Keedy, M. E. Berman, R. Lee, E. F. Coccaro, Neural correlates of aggressive behavior in real time: a review of fMRI studies of laboratory reactive aggression. *Current behavioral neuroscience reports* 4, 138-150 (2017).
11. L. J. Siever, Neurobiology of aggression and violence. *American Journal of Psychiatry* 165, 429-442 (2008).
12. L. Stowers, P. Cameron, J. A. Keller, Ominous odors: olfactory control of instinctive fear and aggression in mice. *Current opinion in neurobiology* 23, 339-345 (2013).
13. R. Zernecke et al., Effects of male anxiety chemosignals on the evaluation of happy facial expressions. *Journal of Psychophysiology*, (2011).
14. W. Zhou, D. Chen, Fear-related chemosignals modulate recognition of fear in ambiguous facial expressions. *Psychological science* 20, 177-183 (2009).
15. B. Klein et al., Activation of the mouse odorant receptor 37 subsystem coincides with a reduction of novel environment-induced activity within the paraventricular nucleus of the hypothalamus. *European Journal of Neuroscience* 41, 793-801 (2015).
16. R. Hoppe, T. D. Lambert, P. B. Samollow, H. Breer, J. Strotmann, Evolution of the "OR37" subfamily of olfactory receptors: a cross-species comparison. *Journal of molecular evolution* 62, 460-472 (2006).
17. C. Verbeurgt et al., Profiling of olfactory receptor gene expression in whole human olfactory mucosa. *PloS one* 9, e96333 (2014).
18. J. D. Mainland et al., The missense of smell: functional variability in the human odorant receptor repertoire. *Nature neuroscience* 17, 114 (2014).
19. B. de Lacy Costello et al., A review of the volatiles from the healthy human body. *Journal of breath research* 8, 014001 (2014).
20. S. K. Jha, N. Marina, C. Liu, K. Hayashi, Human body odor discrimination by GC-MS spectra data mining. *Analytical Methods* 7, 9549-9561 (2015).
21. Y. Endevelt-Shapira et al., Altered responses to social chemosignals in autism spectrum disorder. *Nature neuroscience* 21, 111 (2018).
22. S. P. Taylor, Aggressive behavior and physiological arousal as a function of provocation and the tendency to inhibit aggression 1. *Journal of personality* 35, 297-310 (1967).
23. M. Elson, M. R. Mohseni, J. Breuer, M. Scharkow, T. Quandt, Press CRTT to measure aggressive behavior: The unstandardized use of the competitive reaction time task in aggression research. *Psychological Assessment* 26, 419 (2014).

24. P. R. Giancola, D. J. Parrott, Further evidence for the validity of the Taylor aggression paradigm. *Aggressive Behavior: Official Journal of the International Society for Research on Aggression* 34, 214-229 (2008).

25. P. R. Giancola, S. T. Chermack, Construct validity of laboratory aggression paradigms: A response to Tedeschi and Quigley (1996). *Aggression and Violent Behavior* 3, 237-253 (1998).

26. M. Elson, FlexibleMeasures.com: Competitive reaction time task. DOI: https://doi.org/10.17605/OSF.IO/4G7FV, (2016).

27. P. A. McGrath et al., A new analogue scale for assessing children's pain: an initial validation study. *Pain* 64, 435-443 (1996).

28. G. Gan et al., Reward vs. retaliation—The role of the mesocorticolimbic salience network in human reactive aggression. *Frontiers in behavioral neuroscience* 10, 179 (2016).

29. S. da Cunha-Bang et al., Violent offenders respond to provocations with high amygdala and striatal reactivity. *Social cognitive and affective neuroscience* 12, 802-810 (2017).

30. A. P. Skibsted et al., Aggression-related brain function assessed with the Point Subtraction Aggression Paradigm in fMRI. *Aggressive behavior* 43, 601-610 (2017).

31. T. Allison, A. Puce, G. McCarthy, Social perception from visual cues: role of the STS region. *Trends in cognitive sciences* 4, 267-278 (2000).

32. J. Zaki, K. Hennigan, J. Weber, K. N. Ochsner, Social cognitive conflict resolution: contributions of domain-general and domain-specific neural systems. *Journal of Neuroscience* 30, 8481-8488 (2010).

33. C. L. Harenski, O. Antonenko, M. S. Shane, K. A. Kiehl, A functional imaging investigation of moral deliberation and moral intuition. *Neuroimage* 49, 2707-2716 (2010).

34. R. Kanai et al., Brain structure links loneliness to social perception. *Current Biology* 22, 1975-1979 (2012).

35. K. J. Friston et al., Psychophysiological and modulatory interactions in neuroimaging. *Neuroimage* 6, 218-229 (1997).

SUMMARY OF THE INVENTION

Known methods for managing stress, e.g. medication, aromatherapy, meditation, psychotherapy and others, have known disadvantages. The disadvantages in using medication for reducing stress are various and mostly relate to side effects, e.g. impaired cognitive ability, addiction and abuse. Aromatherapy and meditation require specific environments e.g. a closed room, a quiet area etc., and psychotherapy requires prolonged treatment and the effectiveness can vary between subjects. Therefore, there is a need for a new methodology for managing stress, a methodology that overcomes the disadvantages of existing methods and which can provide a suitable and improved alternative, i.e. can be administered easily, does not require a specific environment, almost immediate effect and has no reported side effects.

In order to detour the inaccuracies associated with correlating stress and various physiological indicators, such as heart rate, the inventors of the technology disclosed herein have developed a novel methodology for determining a state of stress which can be managed by means of the methodology disclosed herein. Stress, particularly perceived stress, has been demonstrated to be reduced or relieved in subjects treated with hexadecanal (herein referred to as HEX). As data shown below demonstrates, use of hexadecanal has exhibited a significantly lower degree of stress and showed no influence on the cognitive performance relative to placebo.

Thus, in accordance with a first aspect of the technology disclosed herein, the invention discloses a composition comprising HEX for use in managing stress, e.g., perceived stress, in a human subject. In some embodiments, the composition consists HEX. In some embodiments, compositions and methods of the invention comprise use of HEX as the sole active material. In some embodiments, excluded from compositions of the invention are other aldehyde compounds such as pentadecanal, and heptadecanal.

The invention further provides use of HEX in a method of managing stress in a human subject in need thereof.

Also provided is a method for managing stress in a human subject, the method comprising administering to the subject an effective amount of HEX to thereby manage stress in the subject. As will be further explained below, the administration of HEX to the human subject, may be active, e.g., through the use of an inhalation device, or passive, e.g., through normal breathing or smelling (or taking in through normal breathing) an amount of HEX in an environment (such as air) containing an amount of HEX.

Hexadecanal, HEX, also known as "olfactory blue" or "OB" has the structure:

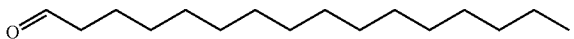 [SMILES: CCCCCCCCCCCCCCCC=O]

The term "stress" refers to a condition or feeling experienced when a subject perceives that demands exceed the personal and social resources the subject is able or expected to mobilize. Thus, within the context of the present invention, the term specifically refers to the subject's perception of stress, a human trait known to be unique to humans, referred to as "perceived stress". Typically, stress originates from some external demand that exceeds one's coping resources. Often stress manifests in pathology or some type of alteration of the environment. In some cases, stress is linked to chronic disease, e.g., metabolic, immune, respiratory, and cardiovascular functioning.

Unlike increased states of anxiety which may be confused with stress in animals, e.g., a laboratory animal, humans have the ability to translate or perceive certain situations as stressful or as stress-causing. Stressful conditions perceived as such by humans are not manifested in the same way in animals. Thus, perceived stress is a unique trait of humans, absent completely in non-human species. While several methodologies have been offered to asses or determine perceived stress, the trait meta-mood scale (TMMS) was designed to assess how people reflect upon their moods, and conceived thus an index of perceived emotional intelligence. The scale has three factors that provide three subscale scores: attention to feelings (relating to monitoring emotions); clarity of feelings (relating to the ability to discriminate between emotions); and mood repair (relating to the ability to regulate unpleasant moods or maintain pleasant moods) (Personality and Individual Differences 47 (2009) 116-121). As demonstrated herein, perceived stress measured according to such a scale, in human subjects administered with HEX according to the invention, has been shown to reduce, to be relieved or diminished without needing to resort to or depend on physiological or pharmacological parameters.

Without wishing to be bound by theory, stress response is regulated through the activation of the hypothalamus-pituitaryadrenal (HPA) axis and sympathetic nervous system (SNS), which intervene concomitantly, since both HPA axis and SNS activity can be reflected by changes in salivary concentrations of proteins such as cortisol and alpha-amylase. Alpha-amylase is one of the major salivary enzymes in humans, and is secreted from the salivary glands in response to sympathetic stimuli. Its concentration in saliva reflects blood levels of catecholamines, particularly norepinephrine. Salivary α-amylase (sAA) is a measure of endogenous adrenergic activity and therefore it is considered as a useful tool for evaluating the SNS activity. IgA is highly sensitive to stress, and its changes are more remarkable than those in salivary cortisol after the same mental stress event. Cortisol is a steroid hormone, secreted from the adrenal cortex via the HPA axis, which increases in response to stressors. Another physiological marker is Heart Rate Variability (HRV) which is commonly used to measure stress in the laboratory.

Aggression, arousal and fear, which may describe animal behavior, may be mistakenly interpreted as stress or mistakenly linked to stress. Thus, "stress" or "perceived stress" as defined herein, exclude displays of aggression, arousal and fear. In other words, the term does not include any display of aggression, namely behaviors that result in personal injury or destruction of property. Although stress and aggression can share some common behaviors, e.g., arousal, the definition of stress herein is aimed at distinguishing between the states of stress and aggression.

As perception of stress is a human trait absent from non-human subjects, thus the term "subject" refers herein solely to a human subject who can experience or perceive his/her present state as stressful. The expression of stress by said human subject may vary between human subjects and may be expressed differently between subjects who are predisposed to suffering from stress or who expect to feel stressful under given conditions. In some embodiments, the subject is at risk of suffering from stress or is one who is predisposed to suffering from stress.

In some embodiments, the subject is generally healthy or suffering from other background pathologies, which may or may not be associated with stress. In some embodiments, the subject does not suffer from autism, and in other embodiments, the subject does not display aggression.

The subject may be a male or a female and may be of any age. In some embodiments, the subject is a male subject.

In some embodiments, the subject is an adult subject (18 years or older). In some embodiments, the subject is a pediatric patient under the age of 18.

Using the active HEX in accordance with the present invention has demonstrated successful management of stress, as defined. As used herein, the term "managing stress" or any lingual variation thereof, refers to the ability of compositions and methods of the invention to treat or prevent or relieve perception of stress, reduce or relieve symptoms which are directly or indirectly associated with stress, or reduce the reoccurrence of stress. By managing stress by way of administering the active, desired pharmacologic and/or physiologic effects may be achieved. The effects can be prophylactic in terms of completely or partially preventing stress or symptom thereof and/or can be therapeutic in terms of a partial or complete cure for stress and/or adverse effect attributable to stress. "Treatment" covers any treatment of stress in a subject, and includes: (a) preventing the stress from occurring in a subject which may be predisposed to stress but has not yet been diagnosed as having it; (b) inhibiting stress, i.e., arresting its development; and (c) relieving stress, i.e., causing regression of stress and/or relieving one or more stress symptoms.

HEX decreases stress, decreases the reoccurrence of stress, decreases the susceptibility of feeling stress and as such decreases the emergence and severity of symptoms that are directly or indirectly associated with stress. The decrease or reduction in stress may be evaluated and quantified by utilizing any given stress assay which measures stress itself or related pathologies as compared to same prior to treatment. The decrease or reduction is by at least 10% of stress measured prior to treatment. In some embodiments, the decrease or reduction is by at least 20%, 30%, 40%, 50%, 60%, 70%, 80% or by 90%. In some embodiments, a decrease embodies complete healing or prevention of stress.

HEX may be administered to a subject at the onset of stress, at any stage during the period of 'feeling stressful', or at any time wherein an uncomfortable feeling of stress may evolve.

Compositions of the invention as well as methods of administering same to a subject comprise an effective amount of the active. The effective amount may be determined by such considerations as may be known in the art. The amount must be effective to achieve the desired effects, some of which mentioned hereinabove, depending, inter alia, on the type and severity the stress episode to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half-life in the body, on undesired side effects, if any, on factors such as age and gender, etc.

While compositions of the invention may be pharmaceutical compositions, nutraceutical compositions, OTC compositions, supplemental compositions or otherwise additive compositions, compositions or formulations comprising HEX may be adapted for any mode of administration. In some embodiments, the mode of administration is by inhalation. As the active does not affect cognitive abilities of the subject, such as measured by memory tests or Stroop test, administration by inhalation has been found advantageous. As used herein, the term "inhalation" comprises any mode of delivery by which an amount of HEX or a composition thereof is delivered to a subject's lungs by breathing or by smelling or be sniffing or generally by taking in an amount of the compound.

Thus, the invention further provides compositions or formulations comprising HEX, which are adapted for inhalation. Apart from the active ingredient, i.e., HEX, these compositions or formulations may further comprise acceptable carriers, vehicles, adjuvants, excipients, or diluents, all well-known to those who are skilled in the art and are readily available to the public. The choice of carrier will be determined in part by the particular method used to administer the composition or the particular method used to inhale the active or the composition comprising it.

In some embodiments, HEX is dissolved in an odorless solvent such as a mineral oil. In some embodiments, the active is dissolved in a solvent, odorless or not (e.g., propylene glycol). In some embodiments, the solvent may be used in combination with a masking agent.

In some embodiments, the amount of HEX in compositions of the invention may be between 0.2 and 2 wt %. In cases where compositions of the invention are adapted for release into an ambient environment, i.e., a volume of air, the amount of HEX may be higher, permitting effective release of HEX into the environment.

In some embodiments, the composition comprising HEX, is provided in a form of an aerosol formulation to be administered via inhalation. The aerosol formulation can be placed into a pressurized acceptable propellant, such as dichlorodifluoromethane, propane, nitrogen, and the like. The composition may also be formulated for non-pressurized preparations, such as in a nebulizer or an atomizer. In some embodiments, the pressurized device, nebulizer or atomizer may be automated.

The aerosol dispersing device can work on its own as well as in conjunction with an HVAC system.

Administration by inhalation may be via such a device as a pressurized receptacle, a nebulizer or an atomizer or by applying the active or a composition thereof onto a skin region to permit inhalation in a continuous or in a per-need mode. Thus, in some embodiments, the active or composition comprising same may be made into a lotion, a crème or any other cosmetic formulation which may be applied to a subject's skin region and subsequently released therefrom to allow a continuous or per-need administration via breathing or smelling. In some embodiments, the active is administered in a form selected from a solid or a liquid contained in a capped vessel, spray, gas, scented cloth, lotion (e.g., cosmetic lotion), crème (e.g., cosmetic lotion), perfume, cologne, scratch-and-sniff odor patch containing microcapsules comprising said hexadecanal, a blister pack containing the active, solid air freshener, air-conditioning potpourri, incense, lightbulb ring, candle, and combinations thereof.

In specific embodiments, HEX can be delivered in the form of a liquid solution, aerosol spray, solid, microcapsules, or via any other suitable form known to deliver a subliminal amount of the active for sniffing by a subject. The active can be administered in combination with an odorless liquid carrier such as mineral oil or water, and can be formulated with a viscosity effective to allow for aerosolization. The hexadecanal can be dispensed, for example, by means of a cloth material that is coated or soaked with the active, as a solid or liquid form contained in a capped vessel, from an aerosol or pump-type spray device, as a nasal spray, by opening a blister pack or scratch-and-sniff odor patch containing the hexadecanal in the form of microspheres, from a pen-like dispenser containing a liquid form of the active adsorbed to a wicking material, and the like.

According to some embodiments, to deliver HEX, the user can employ a device that is portable and minimally disruptive of bystanders. HEX can also be administered to a group of people within a confined area (e.g., vehicle, car), for example, by pumping air containing the active through an air vent, spraying the active into the air as a mist or dry powder using an aerosol or non-aerosol spray, and the like.

HEX can be packaged as a part of an article of manufacture, or kit, for use in stress management. The kit can include in association, for example, an effective amount of the active substance in a non-reactive, biocompatible carrier and/or optional additives as desired such as an antioxidant, preservative, and the like; and means for containing the active such as a vial, jar, pouch, can, bottle, cloth, aerosol can, blister pack, scratch-and-sniff odor patch, pen-like device, and the like. The containing means can include means for spraying by aerosolization or pumping. The kit can further include means for instructing the user about the use of the hexadecanal, in the form of a label or tag attached to the packaging and/or a printed package insert. The parts of the kit can be contained or separately packaged within a packaging material, such as a box or bag.

As inhaling or smelling of HEX has been proven to reduce stress, and since stress affects many aspects of life, the active of the invention may be utilized in a variety of additional indications. Thus, the invention provides use of HEX in achieving one or more health benefits, such as:

increase resilience and reduce vulnerability to illnesses;

decrease or reduce severity of symptoms associated with s disease state;

decrease or reduce symptoms common to diabetic patients;

decrease effect of stress on the evolution of heart diseases;

shortening healing processes;

increasing chances of impregnation;

improving emotional, behavioral, cognitive or physical state;

supporting emotional state or a treatment process or protocol of emotional, psychological or cognitive therapy;

improving cognitive performance;

improving performance under stress related or stress induced situations;

improving sexual performance;

relieving muscles tension;

improving sleep quality;

reducing stress related symptoms like panic attack, asthma attacks, emotional eating, using cigarettes, alcohol, drugs or medications;

supporting quitting smoking, alcohol use, drug and medication abuse and such;

reducing or preventing any of side effects caused by stress or by any of the symptoms caused by stress;

reducing violence or violent demonstrations;

reducing stress in special populations such as prisoners, soldiers' etc;

improving worker's performance.

In some embodiments, any of the above indications or additional uses are embodiments of using the active, as defined herein with respect to compositions and methods of the invention, in managing stress.

In all references herein to an active, the active is HEX.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 4A:
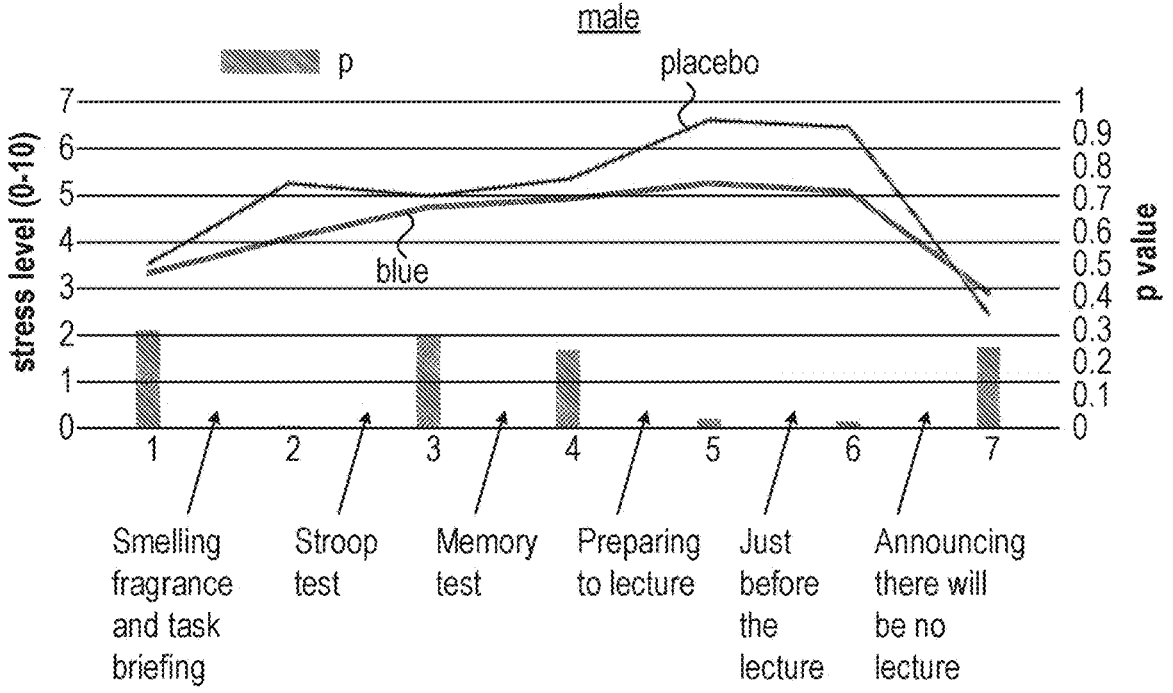
Figure 4B:
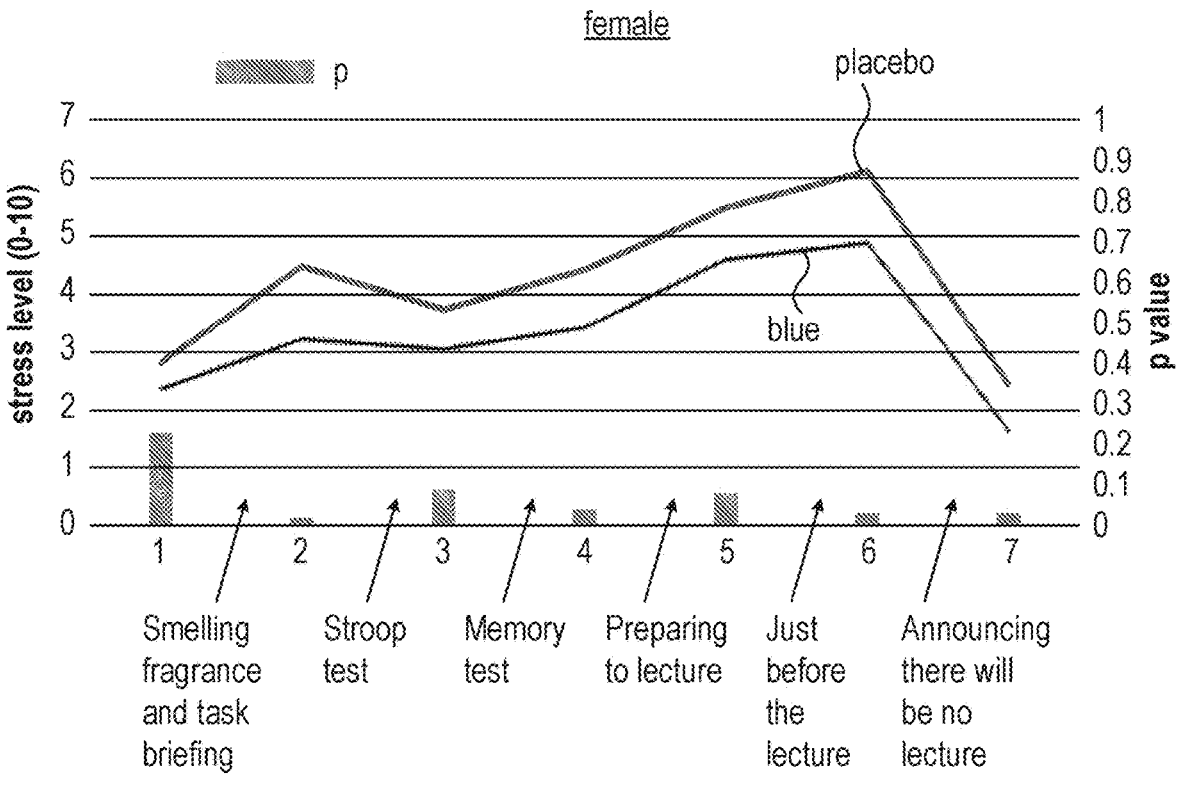

FIGS. 4A-B depict the following: The upper FIG. 4A depicts stress results along the experiment for men. The columns represent p values. The lower FIG. 4B depicts stress results for women.

Figure 5:
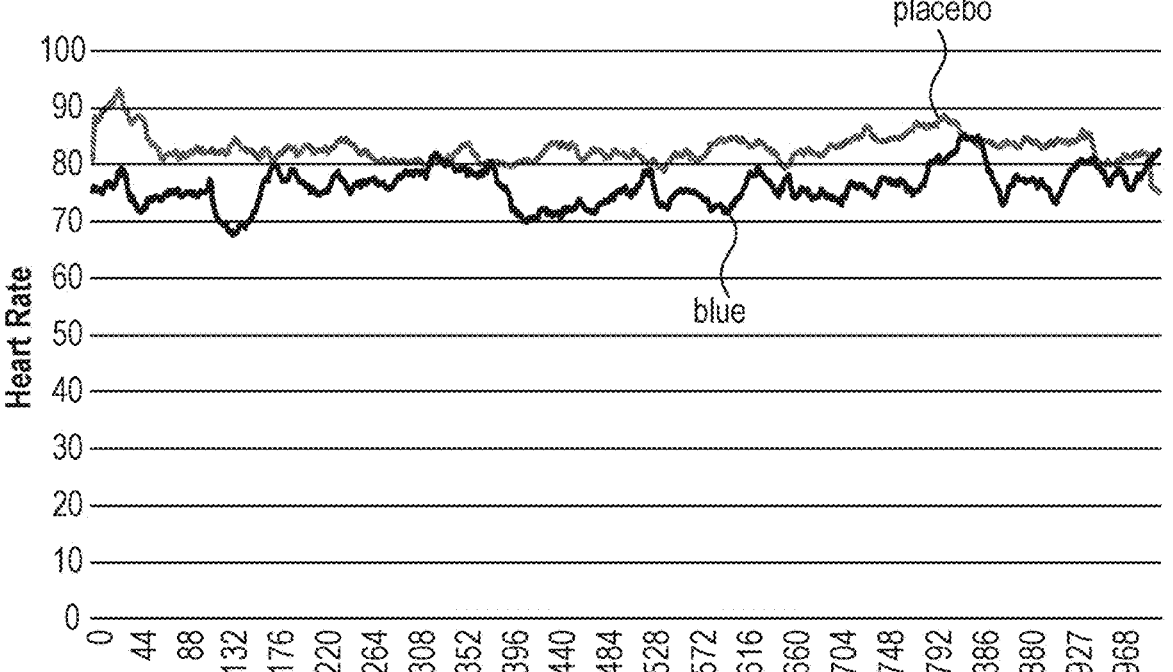

FIG. 5 depicts the average HR along an experiment. The difference across all subject between the conditions is remarkable and statistically significant ($p<0.0001$).

DESCRIPTION OF SPECIFIC EMBODIMENTS OF THE INVENTION

According to the World Health Organization, stress is a significant problem of our times and affects both physical as well as the mental health of people. Stress coping methods are the cognitive, behavioral and psychological efforts to deal with stress, including, but not limited to, medication, aromatherapy, meditation, psychotherapy and others. The disadvantages in using medication for reducing stress are many and mostly related to side effects, e.g. impaired cognitive ability, addiction and abuse. Aromatherapy and meditation require specific environments e.g. a closed room, a quiet area and the like; and psychotherapy requires prolonged treatment and the effectiveness can vary between subjects. Therefore, there is a need for a stress management method and composition which overcomes the disadvantages of the known methods and compositions, i.e. can be administered easily, does not require a specific environment, almost immediate effect and has no known side effects.

Whilst conceiving embodiments of the present invention, the present inventors have uncovered that hexadecanal can be used effectively in stress amelioration without affecting cognitive parameters as assayed by memory tests and Stroop assays.

The ability to manage stress without affecting cognition is central to the development of stress treatment modalities, rendering hexadecanal a promising clinical tool.

As used herein the term "about" refers to ±10%

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Olfactory Blue (Hexadecanal) Test Protocol

Hexadecanal

All three chemicals (Penta-, Hexa- and Heptadecanal) were purchased from TCI Europe. Penta-, Hexa- and Heptadecanal both from TCI were from Caymen (CAS #629-80-1).

As specified by the distributor, Hexadecanal was stored in the freezer at −20° C. For Pentadecanal and Heptadecanal this is not indicated, so they were stored in the fridge at +4° C. The chemicals (in the closed bottle) were transferred to room temperature for 20-30 min for better handling before use. The chemicals were used it either as powder or diluted in 1,2-Propandiol (dissolved at 37° C. with shaking). After use, the chemicals were overlayed in the bottle with N2 to avoid oxidation, sealed in the bottle with parafilm and store at the indicated temperatures.

For experiments 0.083M of Hexadecanal (HEX) dissolved in propylene glycol was used. Heating it for a few minutes eases the process (37° C. is sufficient). The mixture was aliquoted into daily portions, such that we thawed a daily serving prior to experiments. Participants were exposed to 100 ul of 0.083M HEX in 10 consecutive sniffs from a jar, and then taped a band aid with 30 ul on the upper lip. The band aid stayed to assure exposure throughout the experiment. Since propylene glycol has an odor, we used a masking odor.

Another possible diluent is mineral oil that has no perceived odor, so there is no need for a masking odor. The dilution is the same (0.083M).

Protocol for Initial Efficacy Testing

Settings 30 male subjects, 15 using Olfactory Blue (OB—Hexadecanal) and 15 with placebo. Participants were randomly assigned either the OB or placebo conditions (a double blind, between subject designs).

2 experimenters—main experimenter and assistant (to facilitate double blind experiments)

Subjects are exposed to controlled cognitive stressors (manipulations) to raise their stress OB/Placebo is presented to subject to smell before actual test starts.

Double blind experiments—experimenter and subject do not differentiate between OB and placebo.

Experiments conducted in office environment, subject sits in front of computer—all tests are conducted on the computer.

Stress level is monitored through physiological sensors (HR, facial parameters)

Cognitive performance measured through standard cognitive tests—Memory test and Stroop test In addition, subjective feedback is recorded in questionnaire throughout the test—before and after each step.

The entire experiment is video recorded for reference.

Equipment

Computer/laptop with test script and cognitive tests

HR wrist monitor and Central unit

Video camera

2×50 ml identical bottles—one with OB (solvent+Hexadecanal) and one only with dipropylene glycol (DPG)

Goals and KPIs.

The goal of these trials is to validate the efficacy of the Olfactory Blue (OB) in reducing stress without impairing cognitive performance.

KPIs

1. Significant differences between groups in subjective reported stress—lower subjective stress for the OB group.

2. No differences between groups in performance in both tests:

a. Memory test—no difference in number of words recalled between both conditions b. Stroop test—Comparable Stroop effects in both conditions Test Setup Subjects—men only [mean age: 24.97 (SD=1.92)].

An isolated office space (to avoid subject distraction) is prepared with a table and chair.

The computer, Modify standalone and the video recording are positioned and prepared.

Test Running

Subject is introduced and asked to take place in front of computer

Experimenter briefs the subject on the test procedure in general

Subject fills in a consent form (including GDPR consent) and signs the receipt for the money (see form in annex)

Subject fills in personal data on the computer

Experimenter presents the scent bottle (OB or Placebo) given to him by an assistant (who records which bottle has been given) to the subject to smell five sniffs within one minute (2% in the bottle).

Subject is asked about his subjective stress level on a scale between 0 (no stress at all) to 10 (extreme stress)—questionnaire on the computer Experimenter completes the briefing and introduce 3 assignments to the participants: a memory task, a Stroop task and the stress manipulation—subject will have to give a 5 min lecture to an audience on one of three given topics—stressor.

Subject starts the experiment by following instructions on the computer:

1. Subjective stress level

2. Memory test with time limitation—cognitive test #1

3. Subjective stress level

4. Stroop test—cognitive test #2

5. Subjective stress level

6. Subject is given 5 min to prepare lecture

7. Subjective stress level

8. End of experiment

Experimenter debriefs subject—asks for general comments and feeling

Subjective stress level

End of test

Measurements

The following physiological measurements are recorded:

1. HR—heart rate; through a standalone measurement and a HR wrist monitor. The following psychological/subjective measurements are recorded:

2. Memory test—the ability to remember a series of words seen one after the other and after conducting several simple mathematical tasks; scored by counting number of words correctly remembered.

3. Stroop test—the ability to correctly press the colored key corresponding to the colour of the text [Rosenbaum, D., Mama, Y., & Algom, D. (2017). Stand by your Stroop: Standing up enhances selective attention and cognitive control. *Psychological science*, 28(12), 1864-1867].

4. Subjective stress level—the stress level the subject feels at that moment; recorded on the computer.

All data is recorded with clear assignment to the subject, for later analysis. An experimenter assistant confidentially records for each subject the type of scent—OB or Placebo.

Data analysis is performed to result in comparison between the OB group and the Placebo group on the following parameters:

1. HR measurement

2. Score of memory test

3. Score of Stroop test

4. Reported subjective stress level and evolution

OB Experiment—First Results

Figures 1, 2:
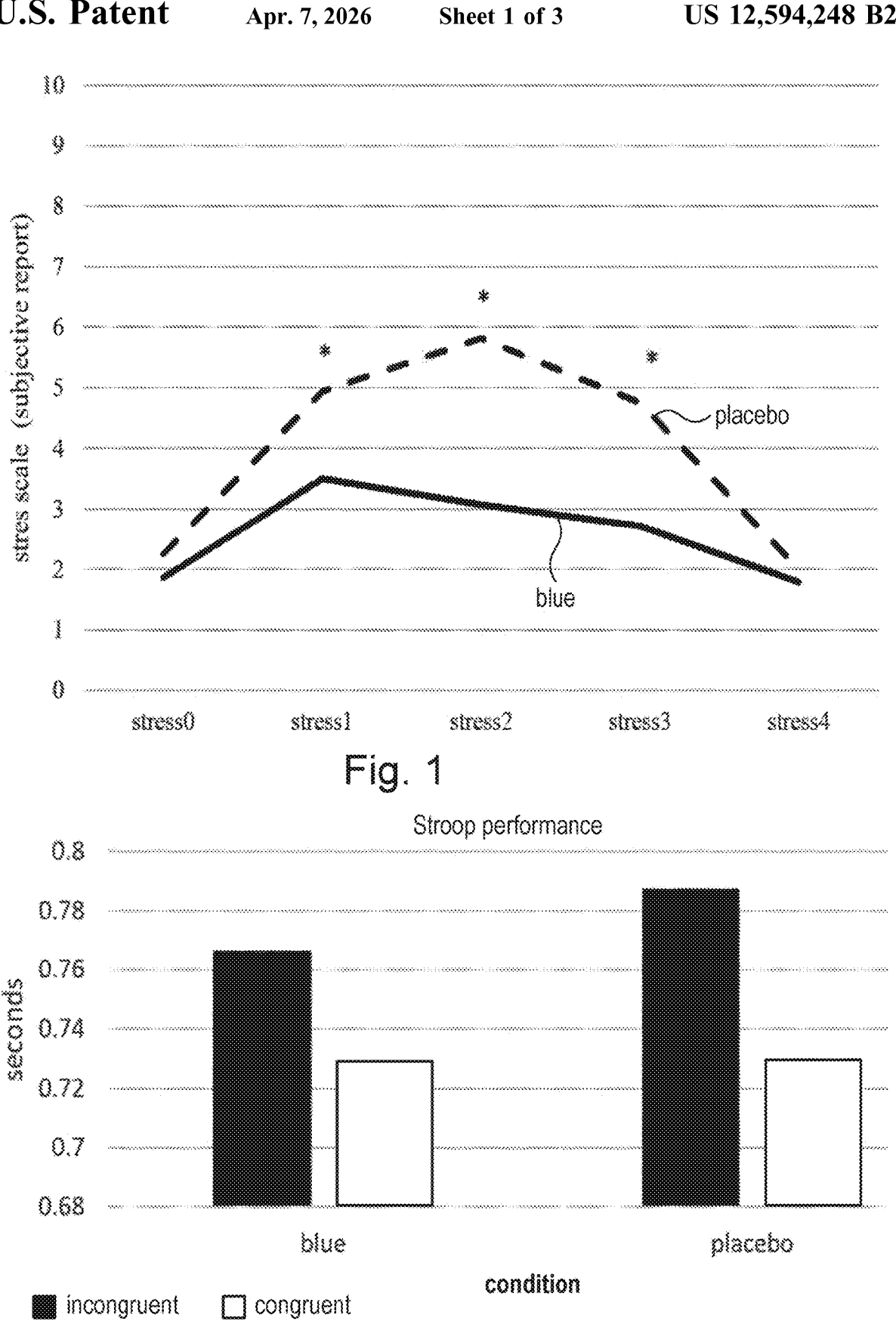
FIG. 1 is a graph showing stress levels of Hexadecanal (named "Blue") treated group vs placebo group.
FIG. 2 is a bar graph showing attention measures by Stroop testing as a measure for cognitive performance in the OB treated group vs placebo group.

FIG. 1 presents subjective stress reports along the experiment and across all participants. The blue columns represent the Blue condition (OB) and the orange columns represent the Placebo condition. Stress scores were from 0 (no stress) to 10 (extreme stress). The asterisks depict significant difference ($p < 0.01$).

*—significant difference ($p < 0.01$)

The X-axis represent five subjective stress reports in different stages of the experiment:

stress0—baseline stress1—after getting assignments (inducing stress) and smelling the substance stress2—after memory test stress3—after Stroop test (just before the lecture)

stress4—end (after being told there will be no lecture)

The results in FIG. 1 show that there was no difference in stress0 (baseline) and stress4 (end) between groups. Blue=DPG (solvent)+hexadecanal. Placebo=DPG (solvent). However, all other reports show highly significant differences between conditions. In all three reports, the Blue group exhibited stress to a significantly lower degree than the Placebo group.

Cognitive Performance:

The use of Hexadecanal does not affect cognitive performance relative to placebo, as evidenced by the Stroop test (FIG. 2). Stroop is the gold standard of attention measurement. No differences were found between blue and placebo conditions, either in reaction time or in number of errors.

Figure 3:
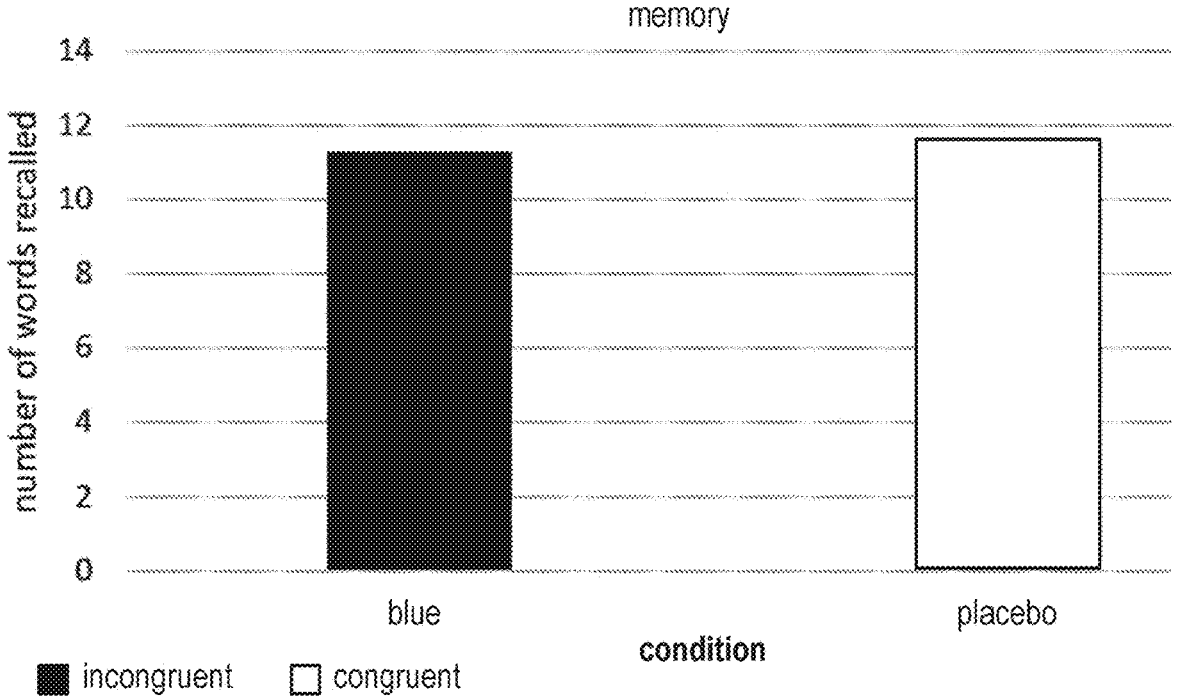
FIG. 3 is a bar graph showing memory parameters as a measure for cognitive performance in the OB treated group vs placebo group.

In a free recall assignment, no differences were found between the conditions (see FIG. 3).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

Example 2

The aim of the study was to test the effect of HEX, previously tested on men, on women subjects.

HEX was found to reduce stress among men, and in the current experiment the study carried out on male subjects was reproduced on women participants.

Sixty-four participants (35 women) with an average age of 27.34 (SD 4.65), half participated in the HEX group and the other half in the PLACEBO group. The study was conducted in Ra'anana, Israel in a rented office using a laptop computer.

Participants came in separately into the Ra'anana office, a research assistant (RA) welcomed them. After a short brief, participants were introduced with a bottle of liquid and were required to smell the bottle for 1 minute (with the instruction to breath normally). After being exposed to the smell, the RA explained about the three tasks (memory, attention, public speaking—the stressor). Participants reported their stress level before and after each assignment (7 times). Just before the last task, participants were informed that this task was canceled and then were asked to report their stress level for the last time.

RESULTS

The first stress report was given pre-manipulation; therefore, it may shed light upon the general stress level of the participants. Mean score for first stress report was 3.32 (SD 1.68) for men and 2.59 (SD 1.76) for women. Four participants (2 women) were excluded from the analysis due to outlier responses: 1 reported she suffers from extreme stage fright, 1 reported she loves to speak in public, 2 reported they were not stressed yet—their stress level reports did not match and were 9-10 throughout the experiment.

A two-way ANOVA was conducted with average stress (measures 2-6) as a dependent variable and gender and fragrance condition as the independent variables. The results show significant main effect for gender as women were significantly less stressed than men (3.61 and 4.44 respectively), $F(1,56)=4.63$, $p=0.03$. Main effect for fragrance was also significant, $F(1,56)=5.1$, $p=0.03$. No interaction was found ($F<0.1$). FIG. 4 shows the stress levels along the experiment. The results clearly support the positive physiological effect of the HEX on stress levels, both for men and women.

FIG. 5 depicts average HR data (for men and women together) which clearly show a difference between the two groups with average HR in HEX group lower than the HR in the placebo group. Both cognitive tests, memory (free recall) and attention (Stroop test) did not differ between the groups.

It seems that the HEX fragrance had a continuous and steady effect on stress both physically (HR) and psychologically (self-repot). The effect seemed to be comparable for both men and women. A decrease in the stress reports after the cognitive tests attest to the importance of the results.

The invention claimed is:

1. A method for managing perceived stress in a human subject, the method comprising administering to the human subject an effective amount of hexadecanal (HEX) to thereby manage the perceived stress in the human subject.

2. The method according to claim 1, wherein said administering step comprises administering the HEX as the sole active material.

3. The method according to claim 1, wherein the managing of the perceived stress is preventing the perceived stress, reducing or relieving symptoms associated with the perceived stress, or reducing reoccurrence of the perceived stress.

4. The method according to claim 1, wherein said administering step comprises administering the HEX with an odorless solvent.

5. The method according to claim 4, wherein the odorless solvent is a mineral oil.

6. The method according to claim 1, wherein said administering step comprises administering the HEX in an aerosol formulation.

7. The method according to claim 1, wherein the HEX is formulated into a cosmetic formulation and said administering step comprises administering the cosmetic formulation of HEX.

8. The method according to claim 7, wherein said administering step comprises applying the cosmetic formulation of HEX onto a skin region of the human subject, whereby the HEX enters lungs of the human subject via smelling of the skin region to which the cosmetic formulation of HEX has been applied.

9. The method according to claim 1, wherein the administering step comprises administering the HEX by inhalation, smelling or sniffing.

* * * * *